(12) United States Patent
D'Angelo, Jr. et al.

(10) Patent No.: US 12,171,893 B1
(45) Date of Patent: Dec. 24, 2024

(54) METHOD, SYSTEM, AND APPARATUS FOR DECONTAMINATION

(71) Applicant: AGarvey LLC, Beavercreek, OH (US)

(72) Inventors: Joseph John D'Angelo, Jr., Beavercreek, OH (US); Sophia Mary Lauwers, Wilmington, OH (US)

( * ) Notice: Subject to any disclaimer, the term of this patent is extended or adjusted under 35 U.S.C. 154(b) by 0 days.

(21) Appl. No.: 17/882,537

(22) Filed: Aug. 6, 2022

Related U.S. Application Data

(63) Continuation of application No. 17/368,585, filed on Jul. 6, 2021, now Pat. No. 11,426,478.

(60) Provisional application No. 63/066,084, filed on Aug. 14, 2020.

(51) Int. Cl.
*A61L 2/10* (2006.01)
*A61L 2/26* (2006.01)

(52) U.S. Cl.
CPC ................... *A61L 2/10* (2013.01); *A61L 2/26* (2013.01); *A61L 2202/11* (2013.01); *A61L 2202/122* (2013.01); *A61L 2202/14* (2013.01)

(58) Field of Classification Search
CPC .......... A61L 2/10; A61L 2/26; A61L 2202/11; A61L 2202/122; A61L 2202/14
See application file for complete search history.

(56) References Cited

U.S. PATENT DOCUMENTS

| | | | |
|---|---|---|---|
| 2009/0189085 A1* | 7/2009 | Rogers | A23L 3/28 426/240 |
| 2020/0384139 A1* | 12/2020 | Ahn | A61L 2/10 |
| 2021/0290799 A1* | 9/2021 | Zhong | A61L 2/14 |

FOREIGN PATENT DOCUMENTS

CN    111388704    * 7/2020

OTHER PUBLICATIONS

English language machine translation for CN111388704 (Year: 2020).*

* cited by examiner

*Primary Examiner* — Sean E Conley

(57) ABSTRACT

An apparatus, system, and method for decontamination.

15 Claims, 12 Drawing Sheets

METHOD, SYSTEM, AND APPARATUS FOR DECONTAMINATION

RELATED APPLICATIONS

This application claims priority to U.S. non-provisional patent application Ser. No. 17/368,585 titled Method, System, and Apparatus for Decontamination, which claims priority to U.S. Provisional Patent Application No. 63/066,084 titled "Method, System, and Apparatus for Decontamination" filed on Aug. 14, 2020, both of which are hereby incorporated in their entirety herein by reference for all purposes.

BACKGROUND

The COVID-19 pandemic has emphasized that it may be beneficial to kill pathogens. The exposure to harmful pathogens is a continuous threat to first responders, health care workers, emergency relief, military personnel, office and craft workers, students, community centers, and travelers. COVID-19 is one example of a widespread dangerous pathogen. The industry to kill or disable reproduction of harmful pathogens includes chemical, heat, radiation, and ultraviolet methods. Each method has benefits and limitations.

SUMMARY

An apparatus, system, and method for decontamination.

BRIEF DESCRIPTION OF THE DRAWINGS

Objects, features, and advantages of embodiments disclosed herein may be better understood by referring to the following description in conjunction with the accompanying drawings. The drawings are not meant to limit the scope of the claims included herewith. For clarity, not every element may be labeled in every figure. The drawings are not necessarily to scale, emphasis instead being placed upon illustrating embodiments, principles, and concepts. Thus, features and advantages of the present disclosure will become more apparent from the following detailed description of exemplary embodiments thereof taken in conjunction with the accompany drawings in which:

DETAILED DESCRIPTION

Figure 1:
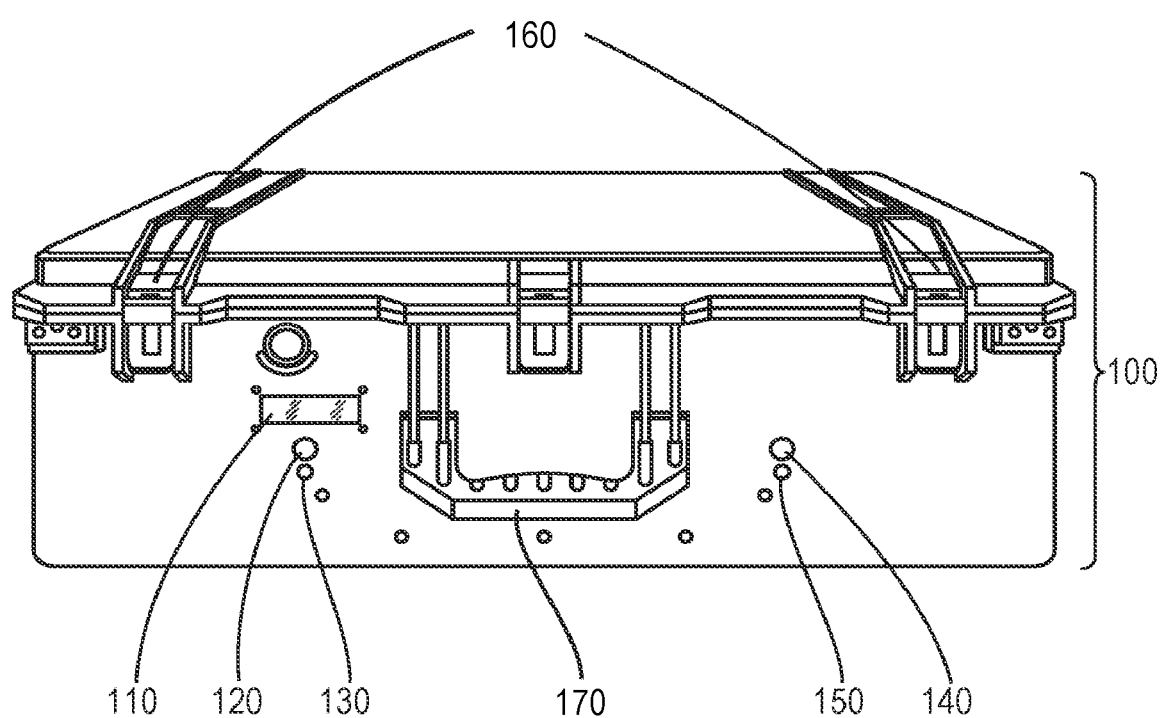
FIG. 1 is a simplified illustration of a Decontamination Unit (DU) with cover closed and control buttons, LEDs and liquid crystal display, in accordance with an embodiment of the current disclosure.

Generally, it may be beneficial to kill pathogens such as viruses and bacteria to limit human exposure to the pathogens. Applicants have recognized that there may be limitations to current techniques of killing pathogens. In most embodiments, Applicants have realized it may be beneficial to use UV radiation to kill or inactive pathogens. In almost all embodiments, Applicants have recognized that UV radiation may also be harmful for humans, which may limit its applicability to kill or remove pathogens. In many embodiments, Applicants have also recognized that there are different types of UV and visible light radiation and each type of radiation may have different characteristics. In some embodiments, Applicants have also recognized that there are techniques to capture and release pathogens in inner layers of personal protective equipment (PPE) and filter media.

Conventionally, UV radiation may be divided into 3 main groups. A first type of UV radiation, UVA, may have the least energy among UV rays. Typically UVA rays may cause skin cells to age and can cause some indirect damage to cells' DNA. Generally, UVA rays are mainly linked to long-term skin damage such as wrinkles, but they are also thought to play a role in some skin cancers. Conventionally, a second type of UV radiation, UVB rays, may have slightly more energy than UVA rays. UVB rays may damage the DNA in skin cells directly and are the main rays that cause sunburns. UVB rays are also thought to cause most skin cancers. A third type of UV radiation, UVC rays, have more energy than the other types of UV rays. A primary source of UVC rays is the sun. Fortunately, because of this, they react with ozone high in our atmosphere and do not reach the ground, so they are not normally a risk factor for skin cancer. But UVC rays can also come from some man-made sources, such as arc welding torches, mercury lamps, and UV sanitizing bulbs used to kill bacteria and other germs (such as in water, air, food, or on surfaces).

In certain embodiments, a system may use Ultraviolet C (UVC) irradiation in combination with electrostatic fields and air movement to improve the decontamination of personal protection equipment, tools, and other artifacts over conventional UVC only systems. In further embodiments, Applicants have recognized that UV light with Mercury bulb with a wavelength of 254 nm, may contain hazardous materials, and this wavelength is not as efficient for absorption by pathogens. In many embodiments, UVC light which is a wavelength of 265 nm which is different from UCA (315-400 nm) and UVB (280-320 nm). In most embodiments, Applicants have realized that 265 nm UVC light may be more efficient for eliminating pathogens because it is absorbed by the pathogens which means that there is a higher rate of decontamination. In most embodiments, UVC may be effective at eliminating pathogens. However, in some embodiments, Applicants have realized that current UVC lights or wands may not be effective in decontaminating a mask or a component of complex geometry. In most embodiments, Applicants have realized that a mask, such as a N95 mask, may be concave in shape which means that just a straight line of UVC light, such as from a wand, may not fully reach all the areas of the masks. In other embodiments, Applicants have realized that for a complex shaped object UVC light, such as from a wand may not fully reach all the areas of masks. In addition, Applicants have realized that with a wand there may be shading of light if a light source is a single fixed point. Current UVC systems that treat N95 masks are single point UVC light systems contained in a square box that treat a single mask or two masks at a time. Current UVC may not sufficiently and efficiently decontaminate masks well.

In some embodiments, Applicants have realized that layered objects such as N95 mask may not be decontaminated by UVC light irradiation only on its surface. Applicants have realized that electrostatic charges may hold particles to inner layers. In certain embodiments, Applicants have realized that mask filtering effectiveness may be improved or decreased by exposing the mask to an electrostatic field. In some embodiments, Applicants have realized that objects may have layers. In other embodiments, Applicants have realized that an interlayer of an object may have a charge. In some embodiments, Applicants have realized that an interlayer of an object may capture particles at least in part fparticle to a charge of the interlayer. In many embodiments, Applicants have realized that protective material, such as a mask, may have a charged interlayer.

In many embodiments, the current disclosure enables a decontamination unit (DU) that may use an array of UVC lights above and below items to treat all surfaces of the items. In some embodiments, a DU may have a reflective material that evenly distributes UVC eliminating shadowing and allowing for all areas of an item such as N95 masks, or objects with complex surfaces such as helmets and hand tools to be treated. In many embodiments, Applicants have realized that portable UVC systems are often heavy and only transportable via wheels from floor to floor within a building. In many embodiments, the current disclosure may enable a DU system that is a light weight with wheels and a handle that can be transported or lifted from floor to floor, building to building, or out in the field. In many embodiments, Applicants have realized that a UV wand may provide UV light in a single plane UVC and may not efficiently treat the complexity of the N95 concave mask or object with a complex shape. In other embodiments, Applicants have realized that Mercury based UV lights may have drawbacks requiring more space for the UVC source and may require longer irradiation times. Typical mercury UVC system irradiate large rooms for long periods of time. In some embodiments, masks may be strung on a clothes line between mercury UVC sources. Conventionally, with a mercury light, people are not allowed in the room while irradiation is in progress. Typically, a room with mercury lights is locked closed after the masks are loaded and the decontamination is started.

In many embodiments, the current disclosure may use one or more UVC LEDS to generate UV light. In some embodiments, the current disclosure may use an array of UVC LEDS to generate UVC light. In most embodiments, UVC LEDS may replace UVA and UVB wavelength for absorption for efficiency. In some embodiments, an array of UVC LED lights may offer better UV radiation to kill or deactivate pathogens. In certain embodiments, an array of UVC LED lights coupled with a reflective material make a more efficient treatment system. In some embodiments, Applicants have realized that decontamination may be improved with air flow through a mask to dislodge particles. In some embodiments Applicants have realized that electrostatic fields may discharge inner layer charges and increase an amount of particles dislodged from inner layers of an object.

In some embodiments, Applicants have realized that decontamination may be improved by increasing the irradiance level with variable duty cycle control. In some embodiments, Applicants have realized that temperature monitoring of the UVC-LEDs may be desirable. In some embodiments, Applicants have realized that UVC-LED irradiance level may require temperature compensation. In some embodiments, Applicants have realized that UVC-LED irradiance output may vary with vibration. In some embodiments, Applicants have realized that UVC-LED irradiance level may require vibration isolation.

In most embodiments, Applicants have realized that typical decontamination units are often in a fixed location and require masks to be sent out and then returned as the decontamination unit may not be moved. In certain embodiments, Applicants have realized that typical decontamination units are large scale units with hazardous materials for treatment. In many embodiments, Applicants have realized that current decontamination units are not made to decontaminate mask such as an N95 mask. In certain embodiments, Applicants have realized that typical decontamination units are simply large heavy cabinets on wheels.

In many embodiments, the current disclosure may enable decontamination without the use of hazardous chemicals. In some embodiments, the current disclosure may enable a DU that is a transportable system that can be a single person lift or roll, placed in a truck and moved to location, can treat one or more masks on site and keeps traceability on personalized PPE.

In a particular embodiment, a UVC LED decontamination unit may be configured for a single UVC LED over a concave side of a N95 mask and four UVC LEDs on the corners of the N95 mask on the convex side of the N95 mask. In some embodiments, a DU may be configured to decontaminate a row of N95 masks. In certain embodiments, a DU UVC LED decontamination unit may be configured for a row of single UVC LED on top-concave side of a N95 masks and four UVC LEDs in a repeating pattern on the corners of the N95 mask on the convex side of the N95 masks. In some embodiments, for rows of N95 masks, a UVC LED decontamination unit may be configured for multiple rows of single UVC LED on top-concave side of a N95 masks and four UVC LEDs in a repeating pattern on the corners of the N95 mask on the convex side of the N95 masks. In some embodiments, a DU may be configured to decontaminate a complex shape such as a helmet. In certain embodiments, a DU UVC LED decontamination unit may be configured for a row of single UVC LEDs on the side of the DU. In certain embodiments, it may be necessary to rotate a complex shaped item to irradiate all sides.

In certain embodiment for rows of N95 masks, a UVC LED decontamination unit may be configured for multiple rows of single UVC LED on top-concave side of a N95 masks and four UVC LEDs in a repeating pattern on the corners of the N95 mask on the convex side of the N95 masks where the UVC LED on the bottom share two UVC LEDs between adjacent masks. In many embodiments, a microprocessor or microcontroller may control the dosage provided by the UVC LEDs. In certain embodiments, UVC LEDs may be pulsed. In some embodiments, UVC LEDs may be powered in groups of three LEDs. In certain embodiments, LEDs may powered with a constant current source. In many embodiments, LEDs may be driven by Pulse Width Modulation.

In some embodiments, LEDS may be driven through a multi-channel switch. In many embodiments, a DU system may be powered by 120 VAC. In certain embodiment, a DU system may be powered by a battery. In many embodiments, a DU unit may be prevented from starting by a hard wired limit switch in a cover of the container. In some embodiments, a DU unit may be prevented from starting by software. In certain embodiments, DC power to LEDs may come from a constant current buck convertor. In some embodiments, a LED may indicate power to UVC LEDs. In some embodiments, a push button may start a decontamination cycle. In certain embodiments, a LED may indicate that a door/cover of a DU is not shut and may prevent operation. In some embodiments, a push button may terminate operation of a DU system. In certain embodiments, a rack may be used to hold masks or object in a specific orientation. In most embodiments, a UVC reflective coating or foil may be applied to inside walls of a container.

In some embodiments, a DU system may have a controllable cycle time for UVC LED emissions. In certain embodiments, a DU system may certify that LEDs intensity hits all locations of a geometric shape. In some embodiments, a DU may accurately provide UVC LED dosage by using a mechanism that acts as a biological indicator showing that enough UVC has been emitted to kill required pathogens. In some embodiments, a DU may have a set UVC emission dosage specific to which pathogen needed to be killed. In some embodiments, a DU may have a user selected interface for choosing such emission dosage specific to pathogen.

In certain embodiments, side walls, top and bottom may be covered with an UVC reflective coating, film or paint to uniformly irradiate ssurface in a DU and on an item being irradiated and to prevent shadowing. In some embodiments, UVC LEDs may be positioned for maximum field of view and UVC coverage to uniformly irradiate surfaces in a DU and on an item being irradiated and to prevent shadowing. In some embodiments, a number of UVC LEDs may be added to increase UVC coverage to uniformly irradiate surfaces in a DU and on an item being irradiated and to prevent shadowing. In certain embodiments, all surfaces of an item may be irradiated.

In some embodiments, UVC LEDs may be positioned to maximize a reflective angle and UVC coverage to uniformly irradiate all surface in a DU and on an item being irradiated and to prevent shadowing. In some embodiments, UVC LEDs may be mounted on a heat sink to maximize irradiated power and extend UVC LED lifetime. In some embodiments, a rack to hold a mask or item being irradiated may be geometrically shaped to prevent or reduce shadowing and increase uniformity of UVC Light irradiation.

In some embodiments, a printed wiring board may be used as a heat sink. In certain embodiments, a rack or holder of an item being irradiated may have features to keep straps or string attached to the item to prevent shadowing. In certain embodiments, a DU may be certified that LEDs intensity hits all locations of the geometric shape of the interior of the DU. In certain embodiments a DU may accurately provide UVC dosage by using a mechanism that acts as a biological indicator showing that enough UVC has been emitted to kill the required pathogens In certain embodiments, a DU case may be chosen to be light enough or small enough that it could be transported by carrying, hand truck or dolly. In most embodiments, a DU may be operated without training using provided instructions for use, quick reference guide, and adhered warning labels. In certain embodiments, a DU may include an on/off switch.

In some embodiments, a DU may have an internal sensor to determine presence of UVC irradiance. In certain embodiments, a DU may contain an internal sensor to determine a relative dosage of UVC irradiance on items. In some embodiments, DU UVC LEDs may be directly controlled by a direct current circuit.

In some embodiments, a DU UVC LEDs may be directly controlled by a pulse circuit. In some embodiments, DU UVC LEDs may be directly controlled by pulse width modulation signal. In many embodiments, DU UVC LEDs may be indirectly controlled by pulse width modulation signal through a multiplexer. In certain embodiments, DU UVC LEDs may be powered continuously while the unit is in operation. In some embodiments, DU UVC LEDs may be powered by a variable duty cycle power source when a unit is in operation. In some embodiments DU UVC LEDs may be powered through a transistor circuit In some embodiments, a DU may have a removable rack. In some embodiments, a DU may be able to tell if a rack is clean. In certain embodiments, cleaning may be performed with a damp cloth. In certain embodiments, a DU may have a liquid crystal display (LCD) to provide status of a decontamination cycle. In certain embodiments, status of a decontamination cycle may be displayed on a Bluetooth device.

In certain embodiments, a status of a decontamination cycle may be displayed on a WiFi device. In many embodiments, a DU decontamination cycle may be controlled by a WiFi device. In some embodiments, a DU decontamination cycle may be controlled by a Bluetooth device. In certain embodiments, a DU decontamination cycle may be controlled by a remote control device. In some embodiments a DU may only operate in a safe mode. In certain embodiments, an item to be decontaminated may be placed on a wire rack. In many embodiments, an item to be decontaminated may be placed on UVC transparent glass. In certain embodiments, UVC transparent materials include UV grade fused silica, quartz, or Sapphire. In other embodiments, UVC transparent materials may be glass like materials which can be cut into rectangles, squares and circles. In most embodiments, but transparent materials may be placed over a UVC LED.

In certain embodiments, an item to be decontaminated may be placed on a hanger. In many embodiments, an item to be decontaminated may be placed on a cradle. In certain embodiment, an item to be decontaminated may be placed on a grill. In certain embodiments, a hook or line or combination may be used to hold and position the mask or object to be decontaminated. In certain embodiments, a revolving platform or attachment may be used to hold, position and rotate a mask or object to be decontaminated. In some embodiment, an item to be decontaminated may be placed on a rotating holder. In many embodiments, a DU may decontaminate high contact surfaces on tools, devices, helmets, any artifact. In certain embodiments, a DU dosage may be determined by a color changing dosimeter.

In certain embodiments a UVC LED may be protected with a UVC transparent cover. In some embodiments, a DU may be able to hold one or more items for decontamination.

In some embodiments, one or more items for decontamination may be held by a system. In some embodiments, a DU may be able to decontaminate a variety of components that are subjected to high person to person contact components (screw driver, wrenches, tooling, PPE).

In some embodiments, a DU may be able to be configured in different geometries, and dimensions to fit to particular components required for decontamination. In some embodiments, items in a DU when placed in a holder or rack may have a geometric shape which creates surfaces out of the way of UVC irradiation that may cause shadowing (such as the string from a mask, or tool handles)

In some embodiments, a DU system may have different modes of activation for decontamination cycles including but not limited to Bluetooth, Wi-Fi, remote control, physical button, interlocking clamps or limit switches. In some embodiments, a DU system may have repetitive mechanisms for safety for a user such as interlocking clamps, limit switches, emergency shutoff points, and auto-stop. In certain embodiments, a DU start switch or button may be embedded in a cover of the system, when the cover is shut the system will start a decontamination cycle.

In some embodiments, a DU may be a design such that a single untrained user could use the system without training or certification (based solely on an instruction for use manual). In some embodiments, a DU may have variable location and number of LEDs dependent upon a component placed in it for decontamination. In certain embodiments, configuration of a DU may be optimized on the geometry of a component, to eliminate shadowing.

In some embodiments, ruggedization may include one or more of the following items; case (military specifications), securing of the components, vibration or isolation pad, shock mounts, double lift handles or wheels for transportation, light weight system, single person carry. In some embodiments, typical decontamination units may be stationary and restricted to a facility they are installed at, such as an office, laboratory, healthcare environment. In many embodiments, a DU system may have an ability to be transported via rail, vehicle or air, and use can be continued due to the integration of ruggedization. In some embodiments, a DU may be used in field with a generator or other energy supply system after transportation. In certain embodiments, a DU internal configuration (UVC LEDs, electronics, power source, etc) may be preassembled on a self-supporting frame.

In certain embodiments, a DU internal configuration (UVC LEDs, electronics, power source) may be preassembled on a self-supporting frame and inserted in a case. In some embodiments, display lights or LEDs may be positioned on the side of a case. In certain embodiments, display lights or LEDs may be positioned on the top of a case. In many embodiments, display lights or LEDs may be positioned on the front of a case In some embodiments, a DU may be ruggedized to survive industrial handling. In certain embodiments, a DU may decontaminate masks in industrial factories, shipyards, on ships, in hospitals, and/or in dentist offices. In some embodiments, an outside of an DU may formed using different shop containers. In many embodiments, a DU may decontaminate in a rectangular container. In some embodiments. a DU may decontaminate clam shell container. In certain embodiments, a DU may decontaminate a circular container.

In some embodiments, a system may have the ability to control UVC dosage admitted to target and kill different types of pathogens. In some embodiments, a user may have a modified dosage level based on pathogen and can choose which level they want to target. In some embodiments a DU may have an air flow around UVC-LEDs and air flow from a face side of a mask through the mask and exit on front side of the mask. In some embodiments a DU may have an air flow around UVC-LEDs and air flow from outside of a mask through the front side of the mask and exit on the inside (face side) of the mask. In some embodiments, a DU may have perforations in a membrane surrounding UVC-LEDs allowing air flow around the UVC-LED and air flow from a face side of the mask through the mask and exit on front side of the mask.

In some embodiments, a DU may have perforations in a membrane surrounding UVC-LEDs allowing air flow around the UVC-LED and air flow from outside of a mask through a front side of the mask and exit on an inside (face side) of the mask. In some embodiments, there may be recirculating air in a decontamination chamber which flows around and through masks. In some embodiments, air flow may be a result of a positive pressure. In some embodiments, air flow may result from a vacuum. In some embodiments, a mask may be discharged by an electromagnetic field. In some embodiments, a mask may be charged by an electromagnetic field causing a layer of layers of the mask to be electrostatically charged. In some embodiments, air flow may cause captured particles to be dislodged from a mask into air in a chamber.

In some embodiments, UVC-LED irradiation may decontaminate air and particles in the air of a chamber. In some embodiments, particles may be equal or greater than 3 microns. In some embodiments, decontamination may result in a log 3 bioburden reduction. In some embodiments, decontamination may result in a log 6 bioburden reduction. In some embodiments, an acoustic method may be used to discharge particle from mask layers. In some embodiments, an ultrasonic method may be used to discharge particles from mask layers. In some embodiments, an interior surface may be coated with a metalized film. In some embodiments, an interior surface may be coated with UVC reflected paint. In some embodiments, an interior surface may be smooth. In some embodiments an interior surface may be rough. In some embodiments an interior surface may be patterned to improve reflection and dispersion of UVC irradiation.

In some embodiments, a system may release particulates such as harmful pathogens from inner layers and exit a mask layer for decontamination. In some embodiments, a system may discharge electrostatic forces holding particles. In some embodiments, a system may force released particles from electrostatic charges. In some embodiments, a system may force larger particle captured by fibers to exit a mask through an outer layer. In some embodiments, system may decontaminate particles discharged from the inner layers as well as mask surfaces. In some embodiments, a system may recharge electrostatic charge on fibers to new/pristine levels. In some embodiments, effectiveness of decontamination may be proven technical feasible by conducting bioburden tests and analysis to prove methods are effective to Log6 reduction. In some embodiments, acoustic/pulsed sound waves may free particles from inner layers. In some embodiments, vibrations of mask from ultrasound may free particles.

Refer now to the example embodiment of FIG. 1, which is a simplified illustration of a DU with cover closed and control buttons, LEDs and liquid crystal display. FIG. 1 is a DU system 100 where the system has the following, a liquid crystal display (LCD) 110 to display status of the decontamination operation, a start button 120 which energizes the UVC LEDs, a run LED 130 which indicates that the UVC LEDs are energized, a stop button 140 which deenergizes the UVC LEDs and a Door open LED 150 which indicated the cover of the system is not closed. The system 100 has latches 160 to tightly close the lid and a carrying handle 170.

Figure 2A:
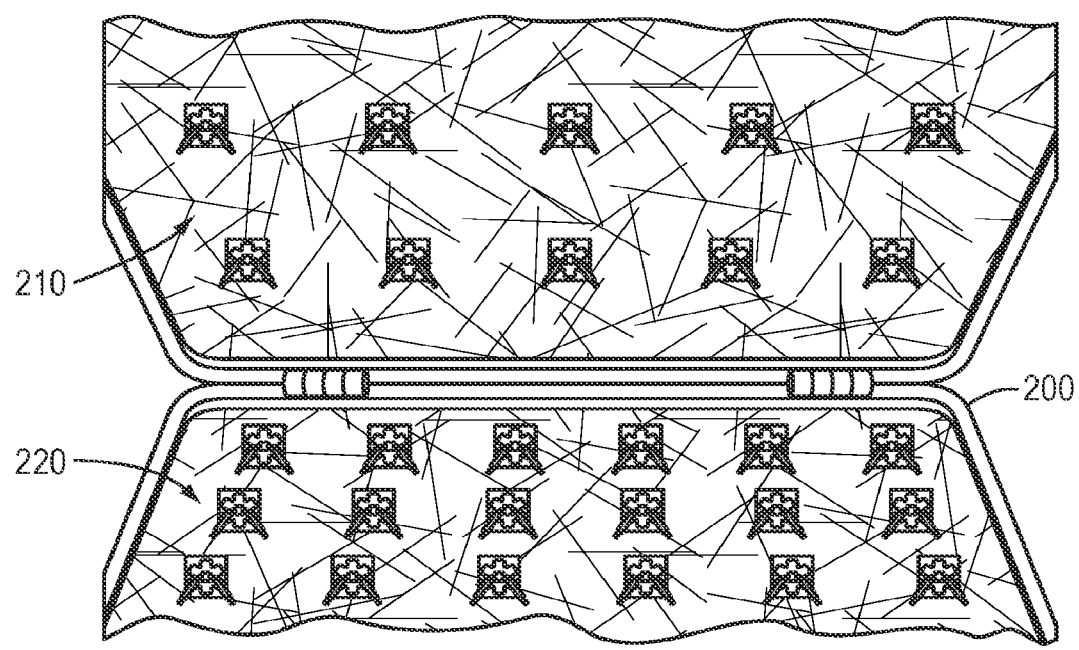
FIG. 2a is a simplified illustration of an open DU showing top and bottom arrays of UVC LEDs which are used to irradiate the object to be decontaminated, in accordance with an embodiment of the current disclosure.

Refer now to the example embodiment of FIG. 2a, which a simplified illustration of open DU 200 showing the top and bottom arrays of UVC LEDs which are used to irradiate the object to be decontaminated. FIG. 2a illustrates a simple embodiment of the top array of UVC LEDs 210 and bottom array of UVC LEDs 220.

Figure 2B:
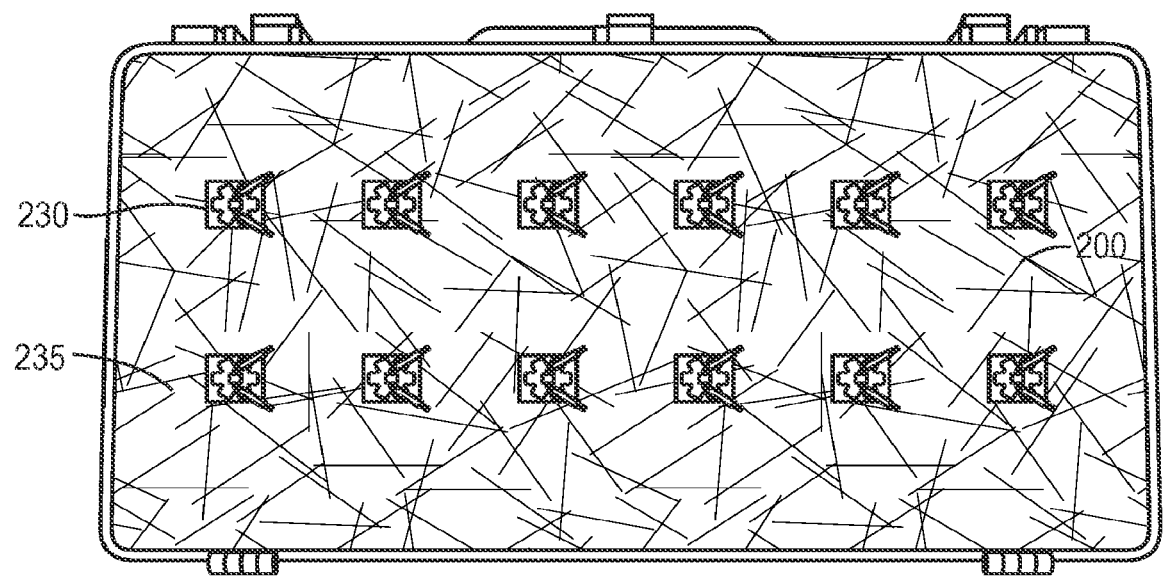
FIG. 2b is a simplified illustration of a top array of UVC LEDs, in accordance with an embodiment of the current disclosure.

Refer now to the example embodiment of FIG. 2b, which is a simplified illustration of a top array of UVC LEDs. FIG. 2b shows a simplified illustration of the arrays of top surface the open DU 200 which includes UVC LEDs 230 and UVC LED 235.

Figure 2C:
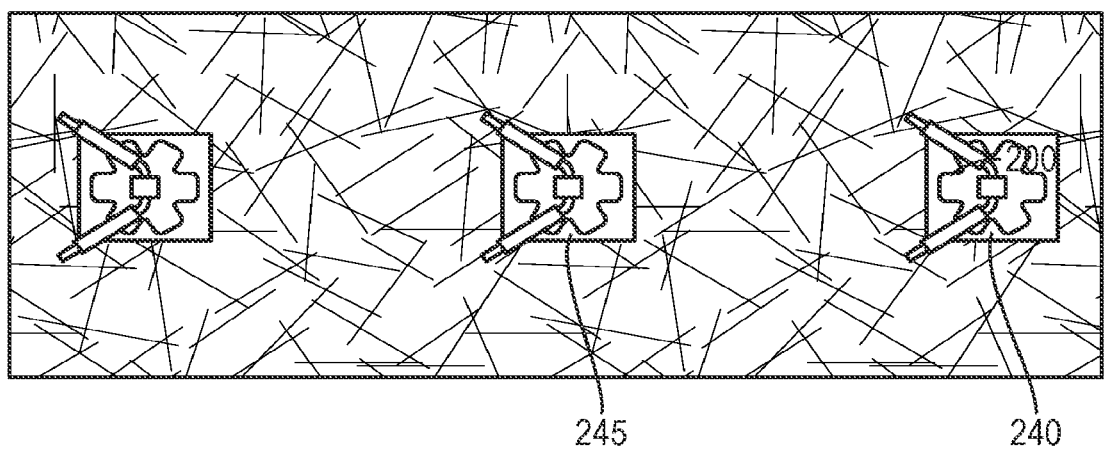
FIG. 2c is a simplified illustration of a top array pattern for three UVC LEDs, in accordance with an embodiment of the current disclosure.

Refer now to the example embodiment of FIG. 2c, which is a simplified illustration of the top array pattern for three UVC LEDs. FIG. 2c illustrates the top surface pattern for three UVC LEDs, two of which are UVC-LED 240 and UVC LED 245.

Figure 2D:
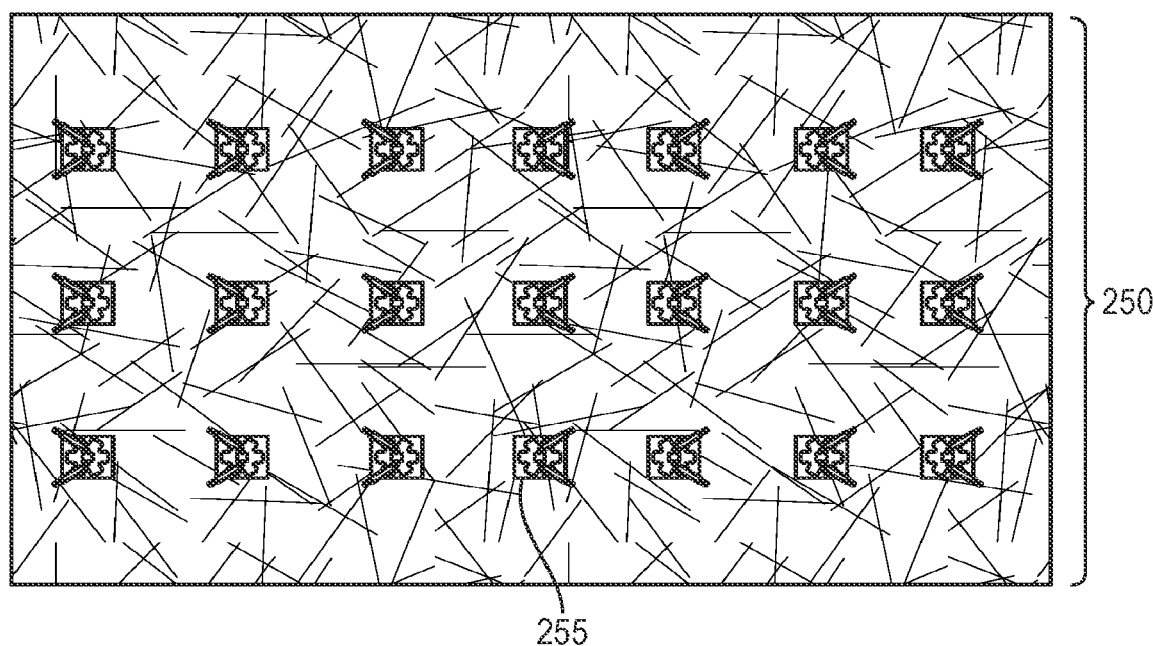
FIG. 2d is a simplified illustration of a bottom array of UVC LEDs, in accordance with an embodiment of the current disclosure.

Refer now to the example embodiment of FIG. 2d, which is a simplified illustration of a bottom array of UVC LEDs. FIG. 2d shows a simplified illustration of the matrix of bottom surface UVC LEDs 250 and the individual UVC LED 255.

Figure 2E:
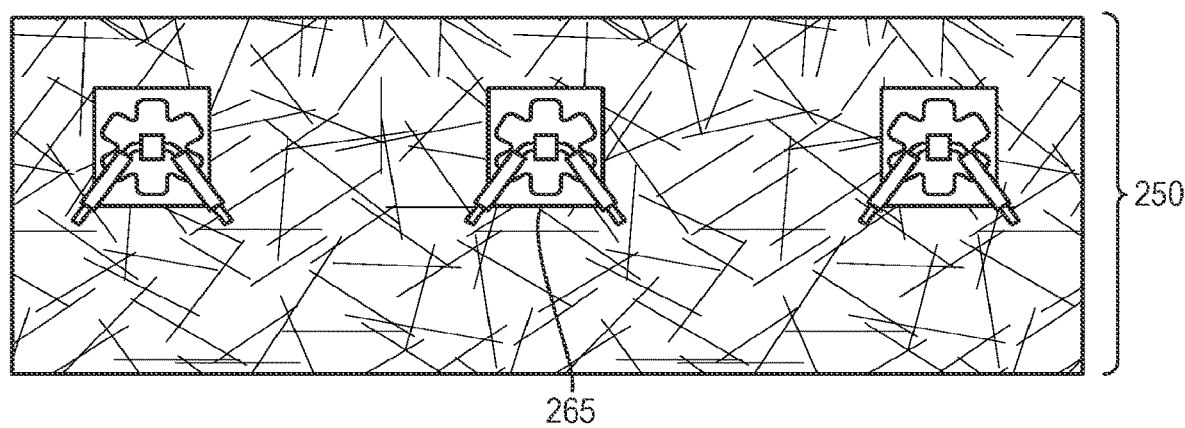
FIG. 2e is an alternative simplified illustration of a bottom array of UVC LEDs, in accordance with an embodiment of the current disclosure.

Refer now to the example embodiment of FIG. 2e, which is a simplified illustration of the bottom array of UVC LEDs. FIG. 2e illustrates the bottom surface pattern for three UVC LEDs of bottom array 250 and the individual UVC LED 265.

Figure 3:
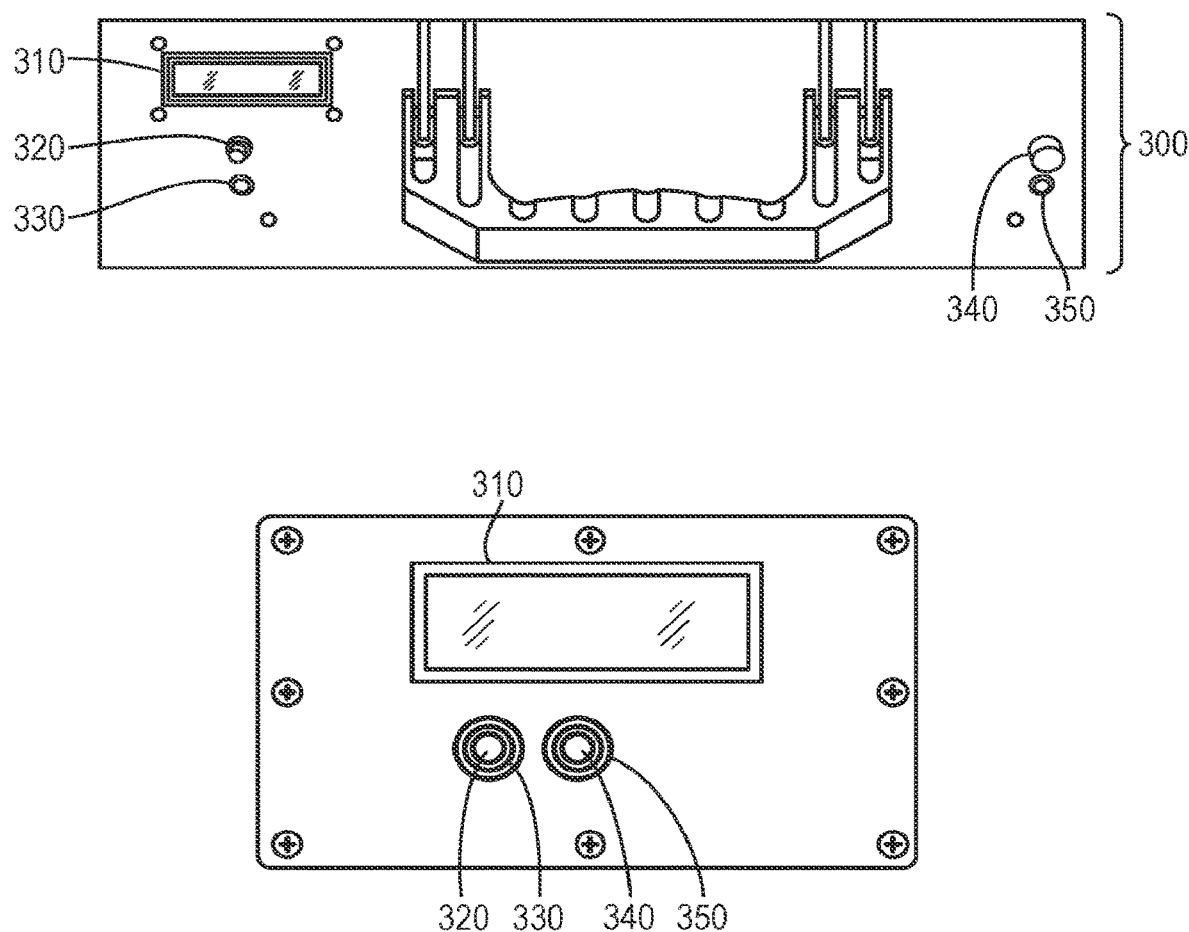
FIG. 3 is a simplified illustration of a front side of a DU illustrating an LCD, Start push button, Run LED, Stop Button and Open Door LED, in accordance with an embodiment of the current disclosure.

Refer now to the example embodiment of FIG. 3, which is a simplified illustration of a front side of the DU illustrating the LCD, Start push button, Run LED, Stop Button and Open Door LED. FIG. 3 illustrates two configuration for the front side of the DU 300 illustrating on the top individually located display LCD 310, discrete Start push button 320, discrete Run LED 330, discrete Stop Button 340 and discrete Open Door LED 350. The bottom illustrates an integrated panel with display LCD 310, combine in one component a Start push button 320 and Run LED 330, combine in one component a Stop Button 340 and Open Door LED 350.

Figure 4:
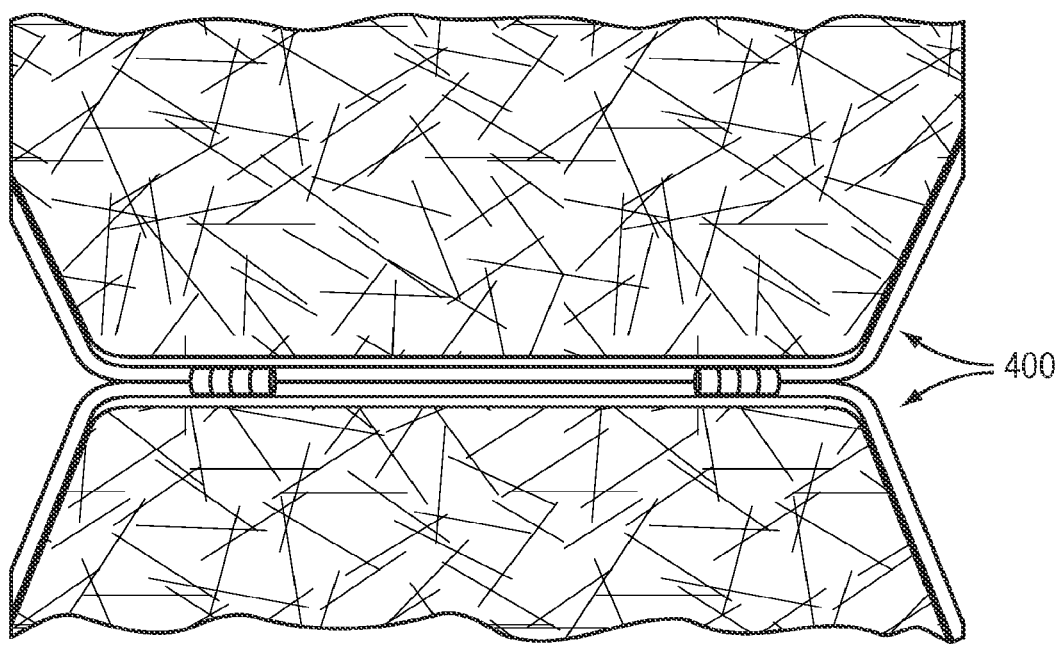
FIG. 4 is a simplified illustration of inside of a DU sides covered with a UVC reflective coating or film, in accordance with an embodiment of the current disclosure.

Refer now to the example embodiment of FIG. 4, which is a simplified illustration of inside of the DU sides covered with a UVC reflective coating or film, in accordance with an embodiment of the current disclosure. FIG. 4 illustrates the simplified embodiment of the interior walls of the DU covered with a UVC reflected coating or film 400. The UVC-LEDs are not illustrated.

Figure 5:
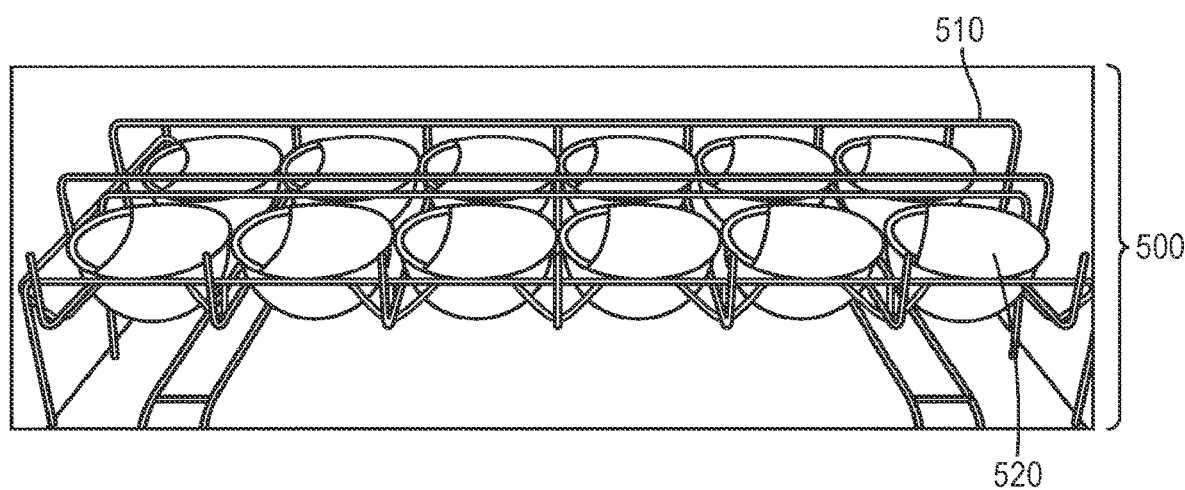
FIG. 5 is a simplified illustration of a rack for holding objects such as masks in a specific orientation, in accordance with an embodiment of the current disclosure.

Refer now to the example embodiment of FIG. 5, which is a simplified illustration of a rack for holding objects such as masks in a specific orientation, in accordance with an embodiment of the current disclosure. FIG. 5 is a simplified illustration showing the embodiment of a rack 500 for holding masks 520 in a specific orientation in rack 510. The rack may be integral to the DU or detachable and formed in any shape to correspond to the object being decontaminated.

Figure 6:
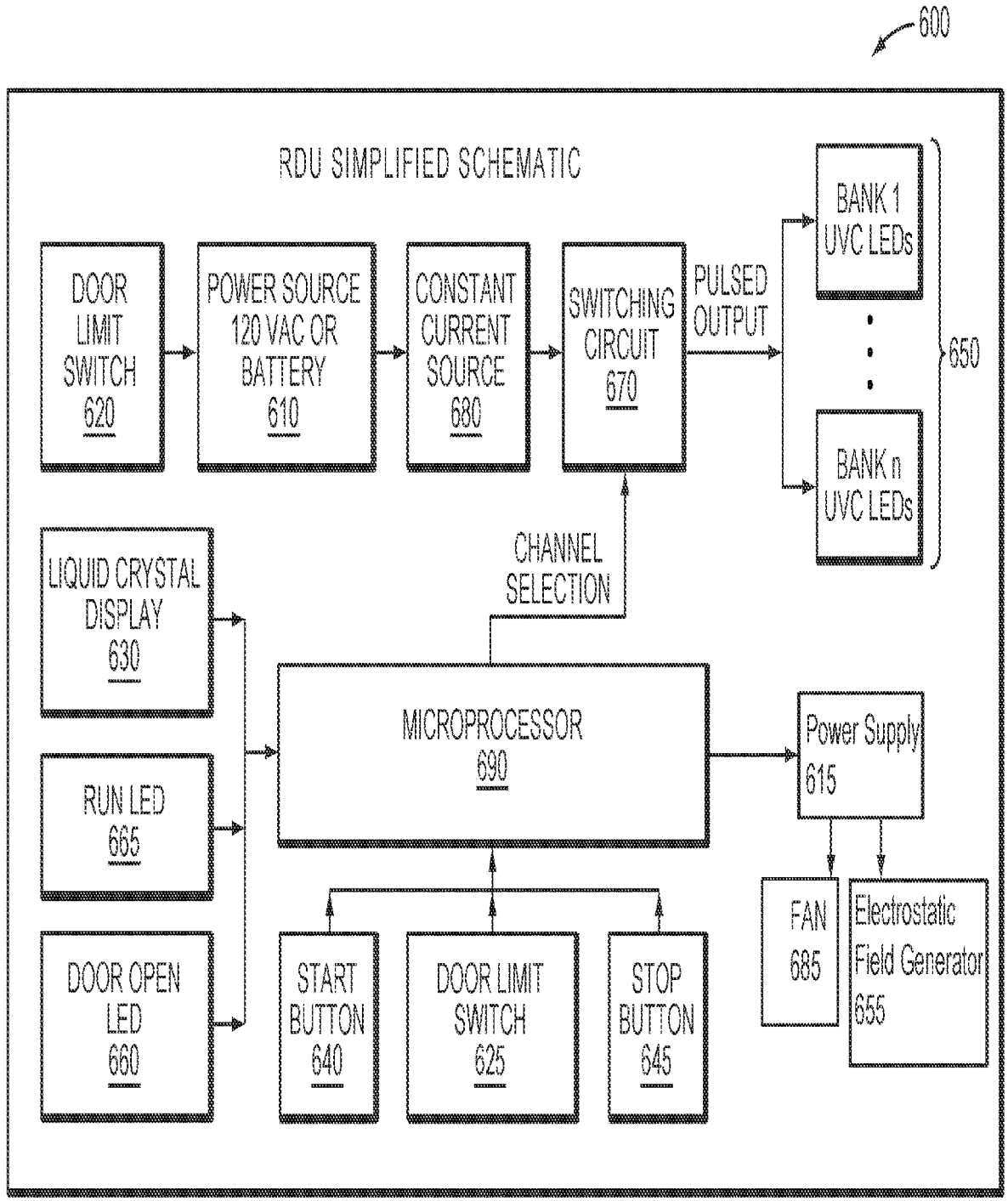
FIG. 6 is a high-level schematic of a control circuit for DU, in accordance with an embodiment of the current disclosure.

Refer now to the example embodiment of FIG. 6, which is a high-level schematic of a control circuit for DU, in accordance with an embodiment of the current disclosure. FIG. 6 show the embodiment of the electronics in a simplified schematic 600 with UVC-LED Power supply 610, door limit switch 620, door limit switch 625, liquid crystal display 630, start button 640, stop button 645, Bank of UVC LEDs 650, door open LED 660, run led 665, switching circuit 670, constant current source 680, microprocessor 690, a power supply for the Electrostatic Field Generator 615, and an Electrostatic Field Generator 655 and a fan 6.

Figure 7:
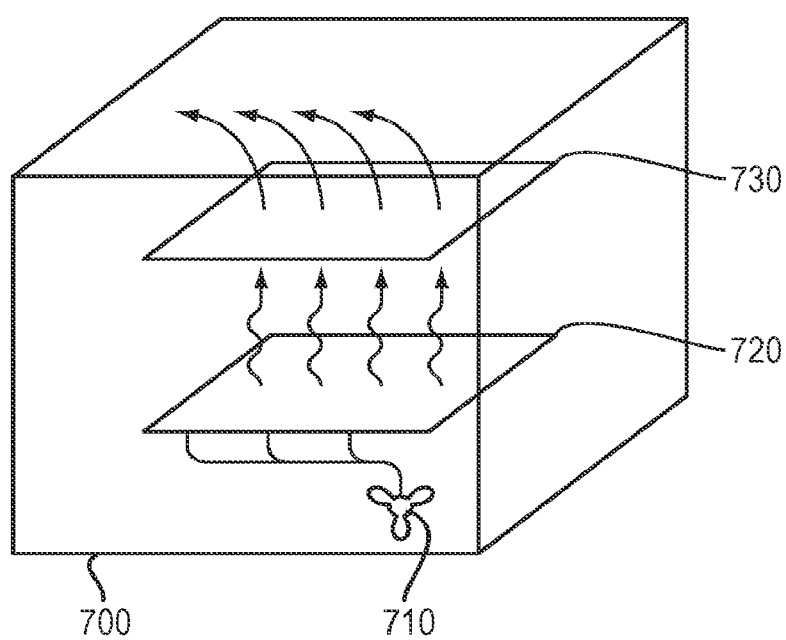
FIG. 7 is a high-level illustration of an air circulation, in accordance with an embodiment of the current disclosure.

Refer now to the example embodiment of FIG. 7, which is a high-level illustration of an air circulation system 700. FIG. 7 shows the embodiment of the bottom layer of UVC LEDs 720 and the top layer of UVC LEDs 730 through which circulating air is pushed by fan 710.

Figure 8:
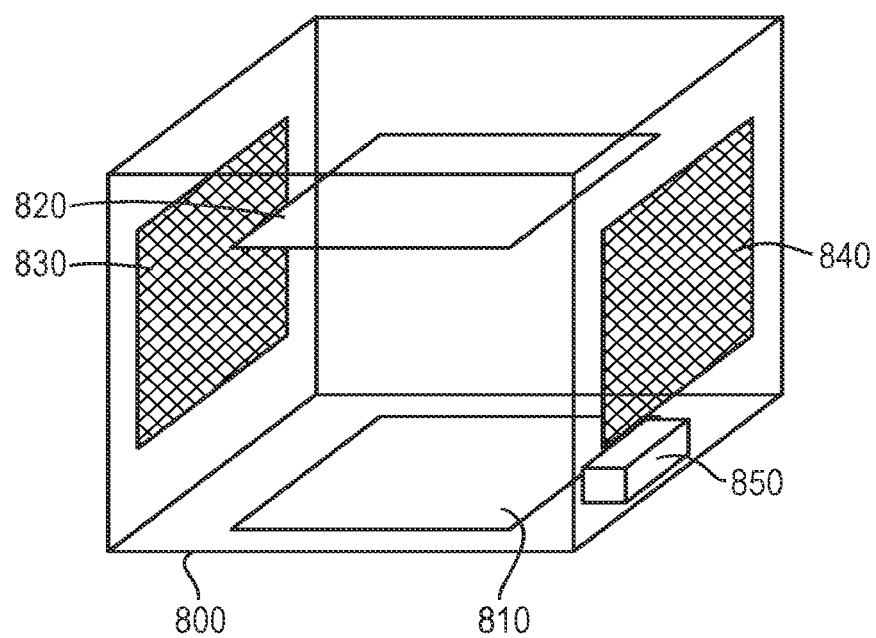
FIG. 8 is a high-level illustration of Electrostatic Field Generator, in accordance with an embodiment of the current disclosure.

Refer now to the example embodiment of FIG. 8, which is a high-level illustration of Electrostatic Field Generator in system 800. FIG. 8 shows the embodiment of the bottom layer of UVC LEDs 810 and the top layer of UVC LEDs 820 above which objects to be decontaminated are radiated by electrostatic field plate 830 and electrostatic field plate 840. Object 850 is the electrostatic power supply for the Electrostatic Field Generator.

In some embodiments, a DU may include a container with a set of LED UV lights; wherein the container has walls; wherein the container has reflective coating applied to the walls of the container; wherein the reflective coating reflects UVC light; wherein the container contains an electrostatic discharge subsystem; where in the container contains an air movement system a power source for the set of UV lights; a pulse circuit electrically connected to the set of UVC LEDs. In many embodiments, a DU may have an electrostatic charge system: an electrostatic discharge system; an air movement system; a vacuum system and an insert for the item to be decontaminated.

In certain embodiments, a DU may have a system to irradiate objects with a dose of UVC light greater than 6 mJ/cm2. In some embodiments a DU may have a container; wherein the container has walls; wherein the walls of the contain have reflective coating. In many embodiments, a DU may have a set of LED UVC lights and a power source for the set of LED UVC light. In certain embodiments, a DU may have an electrostatic charge system, an electrostatic discharge system, and an air movement system. In some embodiments, a DU may have a vacuum system.

In certain embodiments a DU may be ruggedized. In many embodiments a DU may be able to decontaminate pathogens from surfaces of items within the DU. In at least some embodiments, a DU may be ruggedized to survive ground vehicle transportation. In certain embodiments, a DU may have safety mechanism, a start button, and may be enabled to decontaminate multiple PPEs or high surface contact components during a contamination cycle.

In many embodiments, a DU may decontaminate single or multiple masks, and may be enabled to decontaminate other components during a contamination cycle. In some embodiments, a DU may start when a button is pressed after cover of the DU is closed; wherein a failsafe switches enables operation when the cover is closed; wherein the failsafe switch is embedded in a structure of a housing of the DU, wherein the inside of the DU has internal electrical and UVC LED components.

In some embodiments, a DU may be a self-contained unit that can be inserted in a ruggedized container or a standard container. In many embodiments, a DU may have a start button is embedded in the cover of the DU, wherein when a cover of the DU is shut the DU starts the decontamination cycle. In certain embodiments, a DU may treat multiple pathogen types based on the level of UVC dosage provided by the DU. In many embodiments, an exterior shape of a DU container may be selected from the group comprising a rectangular in shape, a clam shell shape, and a circular shape. In some embodiments, a component inside a DU for decontamination may be selected form the group comprising an elongated component; a complex shape for the component; a round component; a clam shell component, and a square component.

In many embodiments, there may be a holding rack to hold components inside the DU. In certain embodiments, a rack may be selected a group comprising a rectangular container; a clam shell container; a circular container; and a custom designed container. In certain embodiments, a component holder may be enabled to hold multiple items in a particular orientation. In at least some embodiments, a component holder may be able to divide components such that surfaces may not be irradiated.

In certain embodiments, a component holder may fabricated from the group comprising a wire mesh, a wire frame, a hook, and a material does not undergo material degradation from UVC light. In many embodiments, a component holder may be selected from a group comprising a stationary system and a system that rotates in the x,y, or z planes. In further embodiments, a component holder may be enabled to hold items in a group comprising PPE, hand tools, or other high surface contact components.

In some embodiments, a DU may include a sensor to sense UVC irradiation to ensure that the system is working properly and an UVC source is releasing emissions. In many embodiments, a DU may include a sensor to monitor leakage of light from the inside to the outside of a container. In most embodiments, a DU may have a sensor to sense relative UVC irradiation levels to measure intensity to ensure decontamination reaches a lethal dosage based on a particular pathogen.

In certain embodiments, a DU may have latches to ensure that a container of the DU is fully closed before operation. In some embodiments, a DU may have limit switches to ensure a container of the DU is fully closed before operation. In other embodiments, a DU may have LED indicators to indicate an active decontamination run and to indicate when a container of the DU is open. In many embodiments, a DU may have a display that notifies users of the status and stage of a decontamination including the group consisting of not running, running, finished, safe to open, load mask, and start cycle. In certain embodiments, a display for a DU may be selected from the group consisting of LCD and LED displays. In some embodiments, a DU may have a display that notifies a user that power is supplied to the DU by a power generation source.

In certain embodiments, a DU may have a constant current source to perform operation. In some embodiments, a DU may have a constant current source to perform operation. In certain embodiments, a DU may change to adjust for temperature. In other embodiments, a DU may be enabled to isolate for vibration. In many embodiments, a DU may have a duty cycle. In other embodiments, a DU may have an output UVC-LED monitoring. In some embodiments a DU may be assembled with UVCs LEDS and electronic building blocks.

In many embodiments, building blocks may be built in different patterns or orientations to satisfy the decontamination of a component of the DU or item placed within the DU. In some embodiments, building blocks may include modular printed circuit boards. In certain embodiments, a DU system may provide uniform UVC LED output. In some embodiments, DU UVC LED lights may be protected with a transparent covering that allows for light of a UVC wavelength to pass through the transparent covering. In certain embodiments, a DU may have a rack; wherein the rack is made from a UVC transparent material UVC transparent materials include UV grade fused silica, quartz, or Sapphire. In some embodiments, UVC transparent materials may be glass like materials which can be cut into rectangles, squares and circles. In some embodiments, cut pieces may be placed over a UVC LED.

In certain embodiments, material for a rack may be selected from the group comprising from a hook or wire mesh and a wire frame. In some embodiments, a fan or air pump may provide air movement around and through masks. In many embodiments, an electrostatic discharge system may discharge electrostatic charges on object layers. In some embodiments, electrostatic charge system may charges electrostatic charges on mask layers.

What is claimed is:

1. A decontamination apparatus for decontaminating a pathogen held on or in an object comprising:
    a decontamination container,
    an object holder to position the object to be decontaminated within the decontamination container, the holder sized to position the object inside the container for decontamination;
    a decontamination source;
    an electrostatic system having a power supply and an electrostatic field generator enabled to charge and discharge the object to be decontaminated; and
    a particle releasing device to sufficiently free the pathogen held by the object to be decontaminated;
    a control system, comprising a microprocessor, the control system having logic programmed to control:
        the electrostatic system to create a first electrostatic field using the electrostatic system to discharge the object to be decontaminated;
        the particle releasing device to sufficiently free the pathogen held by the object to be decontaminated;
        the decontamination source to sufficiently decontaminate a surface of the object including the pathogen; and
        the electrostatic system to create a second electrostatic field using the electrostatic system to charge the object.

2. The decontamination apparatus of claim 1 wherein the electrostatic system has a first electrostatic field plate and a second electrostatic field plate.

3. The decontamination apparatus of claim 1 wherein the control system controls the particle releasing device to generate an acoustic wave.

4. The decontamination apparatus of claim 1 wherein the control system controls the particle releasing device to vibrate the object.

5. The decontamination apparatus of claim 1 wherein the particle releasing device includes a fan that is controlled by the control system to create air movement selected from the group comprising (i) a continuous air movement and (ii) a pulsating air movement.

6. The decontamination apparatus of claim 2 wherein the first electrostatic plate is selected from the group comprising a mesh, a screen, a solid, a line and a plurality of lines of conductive material.

7. The decontamination apparatus of claim 1 wherein the control system controls the particle releasing device to create a vacuum.

8. The decontamination apparatus of claim 1 wherein the decontamination source emits UV radiation.

9. The decontamination apparatus of claim 8 wherein the decontamination source is one or more UV LEDs.

10. The decontamination apparatus of claim 1 wherein the object holder is integrated with the decontamination container.

11. A decontamination system for decontaminating a pathogen held by or in an object comprising:
- a decontamination source;
- an electrostatic field generator having a power supply and an electrostatic field generation system enabled to charge and discharge the object to be decontaminated;
- a particle releasing device to sufficiently release the pathogen discharged from the object to be decontaminated;
- a control system, comprising a microprocessor, having logic programmed to:
  - create a first electrostatic field using the electrostatic system to discharge the object to be decontaminated;
  - sufficiently release the pathogen held by the object to be decontaminated using the particle releasing device;
  - sufficiently decontaminate a surface of the object and the pathogen using the decontamination source; and
  - create a second electrostatic field to charge the object.

12. The decontamination system of claim 11 wherein the control system controls the particle releasing device to generate an acoustic wave.

13. The decontamination system of claim 11 wherein the control system controls the particle releasing device to vibrate the object.

14. The decontamination system of claim 11 wherein the control system controls the particle releasing device to create air movement selected from the group comprising (i) continuous air movement and (ii) pulsating air movement.

15. The decontamination system of claim 11 wherein the electrostatic system has a first electrostatic field plate and a second electrostatic field plate.

* * * * *